United States Patent [19]
Kalchauer et al.

[11] Patent Number: 6,069,266
[45] Date of Patent: May 30, 2000

[54] PROCESS FOR PREPARING ORGANOCHLOROSILANES

[75] Inventors: Wilfried Kalchauer, Burghausen; Herbert Straussberger; Willi Streckel, both of Mehring/Öd, all of Germany

[73] Assignee: Wacker-Chemie GmbH, Munich, Germany

[21] Appl. No.: 09/264,438

[22] Filed: Mar. 8, 1999

[30] Foreign Application Priority Data

Apr. 9, 1998 [DE] Germany .................... 198 16 149

[51] Int. Cl.<sup>7</sup> ........................................ C07F 7/16
[52] U.S. Cl. ............................................. 556/473
[58] Field of Search ............................... 556/473

[56] References Cited

U.S. PATENT DOCUMENTS

| | | | |
|---|---|---|---|
| 2,657,114 | 10/1953 | Wagner | 556/473 |
| 2,672,475 | 3/1954 | Daudt | 556/473 |
| 3,109,014 | 10/1963 | Tamura et al. | 556/473 |
| 3,454,616 | 7/1969 | Ariga et al. | 556/473 |
| 4,864,044 | 9/1989 | Lewis et al. | . |
| 4,962,220 | 10/1990 | Halm et al. | 556/473 |
| 4,966,986 | 10/1990 | Halm et al. | . |

FOREIGN PATENT DOCUMENTS 44 32 896 A1  3/1996  Germany .

OTHER PUBLICATIONS

Lieske et al., "Silicon For Chemical Industry", Geiranger–Norway, Jun. 16–18, 1992, pp. 111–119.
Chemical Abstracts, vol. 93, No. 9, (XP002106845).

*Primary Examiner*—Paul F. Shaver
*Attorney, Agent, or Firm*—Brooks & Kushman P.C.

[57] ABSTRACT

Methylchlorosilanes are prepared by reacting methyl chloride with a contact catalyst which comprises silicon, copper catalyst, zinc promoters and tin promoters and/or antimony promoters, in which hydrogen chloride is added in the course of from 1% to 45% of the duration of the production campaign.

16 Claims, No Drawings

PROCESS FOR PREPARING ORGANOCHLOROSILANES

TECHNICAL FIELD

The invention relates to a process for the direct synthesis of methylchlorosilanes in which hydrogen chloride is occasionally added.

BACKGROUND ART

In the Muller-Rochow direct synthesis, methyl chloride is reacted with silicon in the presence of a copper catalyst and suitable promoters to form methylchlorosilanes, where in addition to a very high productivity (amount of silanes formed per unit time and amount of silicon used), a very high selectivity with respect to the target product dimethyldichlorosilane is also demanded. Dimethyldichlorosilane is required, for example, for preparing linear polysiloxanes.

Despite the high economic importance of the direct synthesis, some of its scientific background has not yet been studied. According to Lieske et al. in Silicone for Chemical Industry, Geiranger-Norway, Jun. 16–18, 1992, owing to the participation of three solids in the reaction, that is to say silicon, catalyst and promoters, the reproducibility of the experiment is frequently poor. In practical conditions, different batches of the direct synthesis proceed with different results despite identical material and reaction parameters.

The direct synthesis can be carried out batchwise or continuously; in industrial production only the continuous variant is used. The continuous direct synthesis is carried out in fluidized-bed reactors in which methyl chloride is used simultaneously as fluidizing medium and reactant. The silicon required is ground in advance to a powder of particle size from 20 to 700 $\mu$m and mixed with copper catalyst and promoters to give the contact catalyst.

A continuous direct synthesis production campaign is begun with the induction phase. At the start of the induction phase, methyl chloride is introduced into the heated contact catalyst. Thereupon the start phase follows, in which the crude silane formation starts. The reaction initially proceeds with low selectivity and reactivity. The stable production phase is then reached. The production campaign ends when methyl chloride is no longer introduced into the contact catalyst.

When a reactor is operated continuously in a production campaign, after a substantially stable production phase, the production rate, based on methylchlorosilanes, and the selectivity, based on the target product dimethyldichlorosilane, decrease. Therefore, the production campaign must be ended after a certain time. A production campaign therefore usually lasts only a few days to several weeks.

The reactor, after completion of a production campaign, is drained, refilled with silicon, copper catalyst and promoters and brought back to reaction conditions. It can be readily seen that the cost-effectiveness of the direct synthesis can be increased by increasing the production rate and also by increasing the duration of the production campaign wherein selectivity remains substantially constant.

Activating the contact catalyst prior to the reaction with methyl chloride by a preliminary reaction with HCl is known. In U.S. Pat. No. 4,864,044 for example, a process is described in which silicon, copper catalyst with or without tin promoter, but in the absence of zinc promoters, can be activated by HCl at approximately 325° C. Among the numerous disadvantages of this type of activation are the following: zinc and zinc compounds may not be added until after the activation, since zinc, with HCl, forms zinc chloride which can readily sublime under the specified reaction conditions; the zinc will thus be removed from the contact catalyst during activation; activation can only proceed prior to the actual reaction with methyl chloride; a separate reactor is required for the activation; the reaction products from the activation, in particular trichlorosilane and tetrachlorosilane are unwanted byproducts of the methylchlorosilane synthesis; and the activation consumes from approximately 1 to 2% of the raw material silicon used.

The addition of HCl to the methyl chloride during the direct synthesis is disclosed, for example, by U.S. Pat. No. 4,966,986. This leads to a considerable change in the crude silane composition, the content of methyldichlorosilane in the crude silane being increased. However, this simultaneously considerably decreases the content of the desired dimethyldichlorosilane.

SUMMARY OF THE INVENTION

It is an object of the present invention to provide a process for the direct synthesis of methylchlorosilanes in accordance with Muller-Rochow in which the productivity can be increased, while retaining selectivity with respect to dimethyldichlorosilane.

DESCRIPTION OF THE PREFERRED EMBODIMENTS

The invention relates to a process for the direct synthesis of methylchlorosilanes by reacting methyl chloride with a contact catalyst which comprises silicon, copper catalyst, zinc promoters and tin promoters and/or antimony promoters, in which hydrogen chloride is added during from 1% to 45% of the period of the production campaign.

HCl can be added during one or more of the induction phase, the start phase and the production phase of the production campaign.

By means of the time-limited addition of HCl during the induction phase and/or start phase of the production campaign, the reactivity in the ensuing production phase can be increased in comparison with the non-activated contact catalyst. By means of a time-limited addition of HCl during the production phase, decreasing reactivities can be increased again, so that in the ensuing phase higher reactivities can again be achieved without addition of HCl.

During the time-limited HCl addition, the reactivity increases, but the selectivity for dimethyldichlorosilane decreases. After the addition of HCl is terminated, the reactivity remains increased and the dimethyldichlorosilane selectivity increases again, however, at least to the value which was determined prior to the addition.

If HCl is added during the start phase, after the addition an increased reactivity and an at least equally high selectivity in comparison with a non-activated production campaign are achieved. In some cases, even higher selectivity values can be measured.

The concentration of HCl in the methyl chloride which is suitable and also the duration of the addition are greatly dependent on the instantaneous state of the contact catalyst with respect to reactivity and selectivity and also on the chosen reaction conditions.

Addition of HCl for too long a period and/or too high a concentration of HCl in the MeCl lead, considered over the entire production campaign, to an increased production of unwanted methylchlorosilanes, such as methyltrichlorosilane or methyldichlorosilane; addition of HCl for too short a period and/or at too low a concentration of HCl in the methyl chloride give only a slight increase in reactivity.

The concentration of HCl in the methyl chloride is, during the activation phases, preferably at least 0.3% by weight, more preferably at least 0.5% by weight, and most preferably at least 0.8% by weight, and preferably at most 5% by weight, in particular at most 3% by weight, in each case based on the mass of methyl chloride.

The duration of an individual HCl addition is dependent on how rapidly the reaction system reacts with respect to the increase in reactivity. The duration can preferably be at least 5 minutes, more preferably at least 20 minutes, and most preferably at least 25 minutes, and preferably at most 10 hours, more preferably at most 5 hours, and most preferably at most 2 hours. Based on a total production campaign, the sum of all the time in which HCl is added is preferably at least 3%, more preferably at least 5%, particularly preferably at least 10% and at most 45%, in particular at most 40%, particularly preferably at most 30%.

Preferably, in the course of a reaction campaign, there are at least 2, in particular at least 3, individual HCl additions. 10 or more individual HCl additions can also take place, for example.

The process is preferably carried out in a fluidized-bed reactor, preferably in the temperature range from 250 to 400° C., in particular at from 250 to 360° C. The process is generally carried out at the pressure of the surrounding atmosphere (that is at about 0.1 MPa) to 0.5 MPa, as this requires the lowest use of resources, but higher pressures can also be employed.

In the process, inert gases such as nitrogen or argon can also be used. Preferably, no inert gas is used.

The rate of the gas stream is chosen in a preferred embodiment in such a manner that a fluidized bed of contact catalyst and gas is formed in the reactor. The mixture of silicon, catalysts and promoters is termed the contact catalyst. Unreacted chloromethane with or without inert gas and the gaseous methylchlorosilanes leave the reactor. If desired, the entrained particles can be separated from the gas stream via one or more cyclones, large entrained particles from the contact catalyst being recycled to the reactor.

The crude silane is then separated off from residual dust contents and unreacted chloromethane and distilled. Purified unreacted chloromethane can be fed back into the reactor.

The contact catalyst is prepared by simply mixing the individual components at room temperature. A subsequent thermal treatment of the contact catalyst in the absence of HCl prior to introducing it into the reactor is possible, but is not carried out in the preferred embodiment.

The process can be carried out continuously or batchwise. Continuously means that the amount of reacted silicon and catalysts and promoters discharged together with the reaction dust are continually replenished, preferably as a premixed contact catalyst.

In the process according to the invention, in a preferred embodiment, silicon of particle size of below 700 $\mu$m and greater than 20 $\mu$m, more preferably of particle size of below 500 $\mu$m and greater than 20 $\mu$m is used. The silicon used usually has a purity of >98%.

In the process according to the invention, use is made of a) copper, preferably in the form of copper oxide mixtures, in the form of copper(II) oxide, in the form of CuCl or in the form of $CuCl_2$. In the case of mixed oxides of the formula $CuO_x$ has a value from 0.6 to 1, preferably a value of at least 0.7. The copper oxides described can be prepared, for example, by the process described in U.S. Pat. No. 5,306,328, in which case the degree of oxidation can be set specifically by the drying temperature and the residence time at this temperature. Preference is given to the use of from 0.5 to 10% by weight, in particular from 0.7 to 7% by weight, of copper catalyst, based on metallic copper and silicon, particular preference is given to from 1 to 5% by weight.

In the process according to the invention, use is made of b) zinc, preferably in the form of metallic zinc, also as an alloy with copper, tin and/or antimony, zinc oxide, or zinc chloride. The amount of zinc used is preferably from 0.5 to 60% by weight, more preferably from 2 to 40% by weight of Zn, based on copper, particular preference being given to the use of from 5 to 30% by weight of Zn.

In the process according to the invention, use is made of c) antimony and/or tin, preferably as metals. The amount of antimony or tin used is preferably from 200 to 8000 ppm, more preferably from 300 to 4000 ppm, based on the copper used, particular preference being given to the use of from 500 to 3000 ppm of antimony and/or tin.

In the examples below, unless stated otherwise, a) all quantities are based on mass;

b) all pressures are 0.10 MPa (absolute);

c) all temperatures are 20° C.;

d) silane M2=dimethyldichlorosilane

The results in the reaction of silicon with chloromethane in the presence of suitable catalysts are dependent not only on the composition of the contact catalyst but also on the structure of the experimental plant and the experimental procedure. To eliminate the two last-mentioned parameters and to be able to demonstrate unambiguously the advantages of the invention, the experiments shown in Examples 1 to 8 were carried out by the following standardized procedure.

Silicon powder is employed as granules from Fesil ASA, Norway, having a particle size in the range from 70 to 240 $\mu$m. The copper oxide is prepared according to U.S. Pat. No. 5,306,328, Example 5. All other chemicals used are commercially available in the chemical industry, e.g. from Fluka Chemie GmbH, Germany.

The experimental plant consists of a laboratory fluidized-bed reactor (vertical glass tube having an internal diameter of 25 mm and a height of 500 mm) having a heating coil, gas-distribution frit, distillation bridge with brine cooling, and receiving flask.

In the standardized procedure used to assess process parameters, 120 g of silicon are intimately mixed with 6 g of copper oxide catalyst, 1 g of zinc oxide and 8 mg of tin powder, charged into the reactor and heated to 340° C. under a nitrogen stream of 40 l/h. 40 l/h of methyl chloride are then passed through the reactor and the contact catalyst is heated to 395° C. After an induction time in the range of from 20 to 30 minutes, the silane formation begins (initiation time), the reaction temperature is decreased to 360° C. and 50 ml of methylchlorosilanes are collected (start phase). All of the HCl additions described in Examples 1 to 4 are made solely during the induction phase/start phase.

In the production phase which follows, a further 30 ml of methylchlorosilanes are then collected. The time for formation of these 30 ml of silanes is termed production phase, and the production rate (PR2) is calculated from the formula $$PR2 = \frac{\text{mg of methylchlorosilanes in the production phase}}{\text{silicon surface area} \times \text{minutes in the production phase}}$$

The silane composition of the 30 ml of methylchlorosilanes was determined by GC analysis in percent by weight.

COMPARISON EXAMPLE C1

This comparison example reflects the reaction course of a non-activated/regenerated contact catalyst. The procedure is in accordance with the standard process without addition of HCl, see Table 1 for the results.

COMPARISON EXAMPLE C2

In this example, HCl is added during the entire reaction course, and the selectivity of silane M2 is greatly decreased. The procedure is in accordance with the standard process with the alteration that HCl was added at a rate of 3 l/h to the methyl chloride during the entire reaction period (this corresponds to about 5% by weight of HCl based on MeCl). See Table 1 for the results.

EXAMPLE 1

This example demonstrates that a time-limited HCl addition at the beginning of the reaction can greatly increase the productivity in the production phase. The procedure is in accordance with the standard process with the alteration that, in the induction phase and in the first 5 minutes of the reaction, HCl is added at a rate of 3 l/h to the MeCl (this corresponds to about 3% of the total reaction period). See Table 1 for the results.

EXAMPLE 2

This example is similar to Example 1, but with the alteration that HCl (2 l/h) was added for 25 minutes (this corresponds to about 15% of the total reaction time). See Table 1 for the results.

EXAMPLE 3

This example demonstrates that a time-limited addition of HCl during the reaction can increase the productivity and the selectivity in the subsequent production phase. The procedure is in accordance with the standard process, with the alteration that the HCl addition (3 l/h) was not started until 20 minutes after the initiation of the reaction and the addition is then carried out for 20 minutes (this corresponds to about 15% of the total reaction time). See Table 1 for the results.

EXAMPLE 4

This example is similar to Example 5, but with the alteration that HCl (1.5 l/h) was added for 40 minutes (this corresponds to about 25% of the total reaction time). See Table 1 for the results.

TABLE 1

| Example | PR2 | % silane M2 |
|---|---|---|
| C1 | 119 | 86.4 |
| C2 | 167 | 73.1 |
| 1 | 140 | 88.1 |
| 2 | 133 | 86.7 |

TABLE 1-continued

| Example | PR2 | % silane M2 |
|---|---|---|
| 3 | 147 | 90.6 |
| 4 | 132 | 91.0 |

EXAMPLE 5 AND COMPARISON EXAMPLE C3

These examples serve to demonstrate that by adding HCl during the production, the reactivity does not decrease as greatly as in a non-activated reaction procedure, and that the addition of HCl does not have a persistently adverse effect on the dimethyldichlorosilane selectivity. Compared with Examples 1–4 and C1 and C2, the procedure was amended as follows, using an experimental plant similar to the previous examples.

120 g of silicon granules from SKW Canada Inc. having a grain size in the range 20–400 µm are intimately mixed with 6 g of copper oxide catalyst, 1 g of zinc oxide and 8 mg of tin powder, charged into the reactor and heated to 340° C. under a nitrogen stream of 40 l/h. 40 l/h of methyl chloride are then passed through the reactor and the contact catalyst is heated to 395° C. After an induction time of 20–30 minutes, the silane formation begins, the reaction temperature is decreased to 360° C. and the methylchlorosilanes formed are collected and analyzed. In Comparison Example C3, the receiver is changed at 90 minute intervals and the mass and composition of the crude silane determined. In Example 5, the receiver is changed after 90 minutes, then HCl is added at a rate of 1.5 l/h (this corresponds to <3% by weight, based on MeCl) for 5 minutes (this period is not taken into account in the tables below). After the addition of HCl is stopped, the receiver is changed again and the reaction run for 90 minutes without HCl addition. HCl addition as specified above then ensued again. This procedure was repeated a plurality of times (see table). The HCl is added during 4% of the total reaction period. The results are presented in Tables 2 and 3.

TABLE 2

| Reaction period (min)[1] | Mass of crude silane (g) Example 5 | Mass of crude silane (g) Comparison Example C3 |
|---|---|---|
| 0–90 | 36.7 | 36.9 |
| 90–180 | 43.1 | 35.0 |
| 180–270 | 42.8 | 28.7 |
| 270–360 | 39.9 | 26.2 |
| Sum | 162.5 | 126.8 |

[1]Does not include HCl addition times.

These examples indicate that addition of HCl increases the silane production by 28%.

TABLE 3

| Reaction period (min)[2] | % by wt. silane M2 Example 5 | % by wt. of silane M2 Comparison Example C3 |
|---|---|---|
| 0–90 | 87.9 | 87.5 |
| 90–180 | 87.8 | 88.1 |
| 180–270 | 88.4 | 87.1 |
| 270–360 | 87.2 | 85.6 |

[2]Does not include HCl addition times.

What is claimed is:

1. In a continuous process for the direct synthesis of methylchlorosilanes by reacting methyl chloride with a contact catalyst which comprises silicon, copper catalyst, zinc promoters and tin and/or antimony promoters, the improvement comprising adding hydrogen chloride during from 1% to 45% of the period of the production campaign of said continuous process.

2. The process as claimed in claim 1, in which the HCl concentration with respect to methyl chloride is at least 0.3% by weight based on the mass of methyl chloride.

3. The process as claimed in claim 1, in which there are at least two individual HCl additions in the course of said reaction campaign.

4. The process as claimed in claim 2, in which there are at least two individual HCl additions in the course of said reaction campaign.

5. The process as claimed in claim 3, in which the duration of an individual HCl addition is at least 5 minutes.

6. The process as claimed in claim 1, wherein addition of hydrogen chloride takes place in an induction phase of said production campaign.

7. The process as claimed in claim 1, wherein addition of hydrogen chloride takes place in a start phase of said production campaign.

8. The process as claimed in claim 1, wherein addition of hydrogen chloride takes place in a production phase of said production campaign.

9. The process as claimed in claim 1, wherein said step of adding hydrogen chloride comprises a plurality of distinct hydrogen chloride additions having a duration of five minutes to ten hours.

10. The process as claimed in claim 1, wherein said step of adding hydrogen chloride comprises a plurality of distinct hydrogen chloride additions having a duration of 20 minutes to 5 hours.

11. The process as claimed in claim 1, wherein said step of adding hydrogen chloride comprises a plurality of distinct hydrogen chloride additions having a duration of 25 minutes to 2 hours.

12. The process as claimed in claim 9, wherein minimally three additions of hydrogen chloride are made.

13. The process as claimed in claim 1, wherein said hydrogen chloride is added during from 3% to 40% of said production campaign.

14. The process as claimed in claim 1, wherein said hydrogen chloride is added during from 5% to 30% of said production campaign.

15. The process as claimed in claim 2, wherein said hydrogen chloride is added during from 3% to 40% of said production campaign.

16. The process as claimed in claim 9, wherein said hydrogen chloride is added during from 3% to 40% of said production campaign.

* * * * *